(12) United States Patent
Raman et al.

(10) Patent No.: US 8,377,480 B2
(45) Date of Patent: *Feb. 19, 2013

(54) GRANULAR SUSTAINED RELEASE PREPARATION AND PRODUCTION THEREOF

(75) Inventors: Siva N. Raman, St. Louis, MO (US); John P. Cunningham, St. Louis, MO (US)

(73) Assignee: Hi-Tech Pharmacal Co., Inc., Amityville, NY (US)

( * ) Notice: Subject to any disclaimer, the term of this patent is extended or adjusted under 35 U.S.C. 154(b) by 131 days.

This patent is subject to a terminal disclaimer.

(21) Appl. No.: 12/850,087

(22) Filed: Aug. 4, 2010

(65) Prior Publication Data

US 2010/0316721 A1 Dec. 16, 2010

Related U.S. Application Data

(63) Continuation of application No. 10/570,242, filed on Feb. 28, 2006, now Pat. No. 7,790,201.

(51) Int. Cl.
*A61K 9/14* (2006.01)

(52) U.S. Cl. .......................... 424/501; 424/489

(58) Field of Classification Search .................... None
See application file for complete search history.

(56) References Cited

U.S. PATENT DOCUMENTS

| | | | |
|---|---|---|---|
| 2,990,332 A | 6/1961 | Keating | |
| 4,221,778 A | 9/1980 | Raghunathan | |
| 4,690,933 A | 9/1987 | Coker et al. | |
| 4,695,467 A | 9/1987 | Uemura et al. | |
| 4,762,709 A | 8/1988 | Sheumaker | |
| 4,847,077 A | 7/1989 | Raghunathan | |
| 4,859,461 A | 8/1989 | Chow et al. | |
| 4,892,738 A | 1/1990 | Takagishi et al. | |
| 4,894,239 A | 1/1990 | Nonomura et al. | |
| 4,959,219 A * | 9/1990 | Chow et al. | 424/480 |
| 4,996,047 A | 2/1991 | Kelleher et al. | |
| 5,071,646 A | 12/1991 | Malkowska et al. | |
| 5,102,668 A | 4/1992 | Eichel et al. | |
| 5,200,193 A | 4/1993 | Radebaugh et al. | |
| 5,275,820 A | 1/1994 | Chang | |
| 5,482,718 A | 1/1996 | Shah et al. | |
| 5,783,212 A | 7/1998 | Fassihi et al. | |
| 5,968,551 A | 10/1999 | Oshlack et al. | |
| 5,980,882 A | 11/1999 | Eichman | |
| 6,001,392 A | 12/1999 | Wen et al. | |
| 6,077,532 A | 6/2000 | Malkowska et al. | |
| 6,228,398 B1 | 5/2001 | Devane et al. | |
| 6,280,717 B1 * | 8/2001 | Kamakura et al. | 424/78.1 |
| 2002/0031490 A1 | 3/2002 | Bellamy et al. | |
| 2002/0173487 A1 | 11/2002 | Backenfeld et al. | |
| 2003/0170301 A1 | 9/2003 | Wehling | |
| 2006/0286174 A1 * | 12/2006 | Raman et al. | 424/489 |

FOREIGN PATENT DOCUMENTS

| | | |
|---|---|---|
| EP | 0 254 811 | 2/1988 |
| EP | 0 254 822 | 2/1988 |
| EP | 278464 A1 * | 8/1988 |
| EP | 320519 A1 * | 6/1989 |
| FR | 2 705 677 | 12/1994 |
| WO | WO 92/11038 | 7/1992 |
| WO | WO 02/49675 | 6/2002 |

OTHER PUBLICATIONS

Remington: the science and practice of pharmacy, 20th edition, 2000, p. 870-871.*
Tousey, M.D. Pharmaceutical Technology, p. 8-13, Oct. 2002.*
Nujoma et al., "A Designer's Polymer as an Oral Drug carrier (Tablet) with Pseudo-Zero-Order Release Kinetics", J. Pharm. Sci., 85(10), 1996, pp. 1091-1095.
Anand et al., "Ion-exchange resins: carrying drug delivery forward", Drug Discovery Today (DDDT), 6(17), 2001, pp. 905-914.
AG® 50W-X8 Resin from Bio-Rad MSDS Printed Oct. 28, 2008.
Amberlite IRP69 (Sodium Polystyrene Sulfonate USP) Product Data Sheet Feb. 2006, pp. 1-4.

* cited by examiner

*Primary Examiner* — Nissa Westerberg
(74) *Attorney, Agent, or Firm* — Armstrong Teasdale LLP

(57) ABSTRACT

There is disclosed a novel sustained release granular resin-pharmaceutical composition comprising an ion exchange resin complexed with a pharmaceutical material wherein said complex is embedded into and on the surface of a diffusion barrier material. There is also disclosed a novel process for preparing the granulated complex wherein an aqueous granulating vehicle is employed to form the complex and the granulated product, thereby avoiding the use of coatings and large amounts of organic solvents in the process.

23 Claims, No Drawings

GRANULAR SUSTAINED RELEASE PREPARATION AND PRODUCTION THEREOF

CROSS REFERENCE TO RELATED APPLICATION

This application is a continuation of U.S. patent application Ser. No. 10/570,242 filed Feb. 28, 2006, which is incorporated herein in its entirety.

BACKGROUND OF THE INVENTION

This invention relates to granular sustained release particles containing pharmaceutical material.

An early disclosure of sustained release pharmaceutical preparations appears in U.S. Pat. No. 2,990,332 to Keating wherein a sulphonic acid cation exchange resin is employed. A pharmaceutical is ionically bonded or adsorbed onto an ion exchange resin particle. One requirement of the pharmaceutical is that it contains a basic functional group.

Thereafter, ion exchange resin drug complexes were provided with a diffusion barrier coating that provided delayed action by the gastric juices of the person being treated with the drug. An early example of such preparations is U.S. Pat. No. 4,221,778 to Raghunathan wherein the resins provided were various polymeric matrices including AMBERLITE IR120, a cationic exchange resin as well as AMBERLITE XE69, which is a smaller sized resin particle derived from AMBERLITE IR120. Other ion exchange resins mentioned were methacrylic, acrylic, phenol formaldehyde ion exchange agents with cellulosic or dextran polymer matrices and inorganic ion exchange matrices. In the '778 patent, ethylcellulose was employed as a water-permeable, diffusion barrier coating over the ion exchange resin particle.

There followed numerous publications wherein the ion exchange resins were treated with hydroxypropylmethyl cellulose, hydroxypropyl cellulose, sorbitol, hydroxypropyl sorbitol and polyvinylpyrrolidone. One example of this is U.S. Pat. No. 4,859,461 to Chow et al. Varying the thickness of the polymeric coatings provides the duration of extended release. A variation of the organic coating of the resin particle is disclosed in U.S. Pat. No. 4,894,239 to Nonomura et al. In this patent a water permeable layer is applied to the resin particle. In one example dihydrocodeine phosphate was converted to the free base in ethanol and combined with a cation exchange resin. The loaded resin was then separated, dried and then coated with aminoalkyl methacrylate in acetone. An eight-hour release pattern was produced by this particle.

Another approach to sustained release medication is found in U.S. Pat. No. 5,968,551 to Oshlack and Chassin, wherein a unit dose of opioid is provided by constructing an array of different sized particles ranging in size from 0.1 mm to 3 mm. In some embodiments spherical particles are provided but then coated with materials such as ethylcellulose or water-soluble cellulose such as hydroxy lower alkyl cellulose. Various solvent coating processes are disclosed. In addition, a melt pelletization method is disclosed wherein the opioid is combined with a binder and other optional ingredients. The binder material containing the opioid is then pelletized with a high shear mixer to obtain the required sizes.

Another process is described in U.S. Published Application 2002/0031490. The process is based upon a resin that can be hydrated with a small amount of water whereby the resin absorbs the active material that is relatively insoluble in the amount of water employed. In this system the active is at least partially dissolved in a solvent. Thus, a solvent system is also disclosed wherein the hydrated resin is dispersed in a solvent for the active. Solvents include organic solvents such as ethanol, dichloroethane and 1,1,1,2-tetrafluoroethane.

Other examples of various sustained release formulations involving coated resin particles include U.S. Pat. Nos. 6,001,392; 6,228,398; 4,996,047; 4,959,219; 4,847,077; 4,762,709; 4,690,933 and EP 911 039.

The prior art has disclosed sustained release compositions and processes that include a coating or coating step. It would be advantageous to provide a sustained release pharmaceutical particle by a process that does not require a polymer film coating for controlled drug delivery because such processes are lengthy and expensive.

SUMMARY OF THE INVENTION

In accordance with this invention, there is provided a pharmaceutical containing sustained release ion exchange resin particulate material produced by a process that does not require a coating. The sustained release particles of this invention comprise an ion exchange resin complexed with a pharmaceutical material embedded in and on the surface of a granulated particulate diffusion barrier material combined by means of a granulation process.

Rather than a continuous coating of the complex, the sustained release particles of this invention comprise a diffusion barrier material comprising particles of granulated diffusion material having the particles of pharmaceutical resin complex embedded into and on the surface of the diffusion barrier material. The diffusion barrier material is combined with the ion exchange resin complex in a granulation process relying upon shear forces acting on the complex and particles that form the diffusion barrier material. The granulated particulate sustained release material of this invention is provided by combining a pharmaceutical material with an appropriate ion exchange resin particle by typical means and then depositing these particles into and on the surface of a granulated, particulate diffusion barrier material by means of a granulator employing a granulating vehicle. In one embodiment of this invention, the sustained release pharmaceutical particles can be provided in spherical form after granulation is completed, without performing a further step for spheronization. Appropriate screening techniques known in the art can provide the desired particle size.

The sustained release particles of this invention provide medication in the body of a mammal for an extended period such as, for example, a period of about eight hours although other release times may be provided. Various release times are available by the process of this invention by varying drug loading of the resin, and by varying the type and amount of diffusion barrier material employed in the particle as will be more fully disclosed below.

DETAILED DESCRIPTION OF THE INVENTION

As is known in the art, ion exchange resin particles can react with active pharmaceutical materials to form complexes. A cation exchange resin can form a complex with drugs containing a basic component while an anion exchange resin can complex with drugs containing an acidic component. Generally, the drug is mixed with an aqueous suspension of the ion exchange resin and the complex is dried. The amount of pharmaceutical complexed to the resin may be detected by a change in solution pH, by other changes in physical properties of the complex or by a decrease in concentration of drug dissolved in the aqueous phase.

Cationic drugs are positively charged and tend to displace the cationic groups, typically becoming complexed to the resin by ionic bonds. Since basic drugs are generally cationic, cationic exchange resins are often used to prepare drug-resin complexes with basic drugs. Typical approaches to forming a water insoluble drug-resin complex are to react the sodium salt of a cationic ion exchange resin with a cationic drug or to react the base form of the drug with the acid form of the cationic ion exchange resin.

Any number of different ion exchange resins may be successfully employed in the novel practice of this invention. The ion exchange resin chosen should not be toxic to humans and generally should not interfere with the medicinal effect of the pharmaceutical material. Ion exchange resins known to be useful in the present invention are AMBERLITE IRP69 (a trademark of Rohm & Haas Chemical Co.) and the like. This resin is a gel type divinylbenzene sulfonic acid cationic exchange resin. Both cationic and anionic exchange resins may be employed in the products and processes of this invention. Suitable resins for the practice of the invention include functionalized resins derived from divinylbenzenes, styrenic, methacrylic, methacrylamide, acrylic, acrylamide, carbacrylic, phenol-formaldehyde, polyhydroxy resins, polycarboxylic, carboxyvinyl, cellulosic, and dextran polymer resins. Amphoteric resins, i.e., those derived from the above monomers but containing both anionic and cationic sites in the same polymer may also be used. Zwitterionic resins may also be used in the practice of the present invention. The size range of the resin particles employed in this invention varies depending upon the type of resin employed. Such resin size ranges typically from US Std. Mesh of about #10 to about #400, or #100 to #400 (150-37 microns).

Any number of pharmaceutical active ingredients that can exist in ionic form in a semi-polar or polar solvent, such as water, are a potential candidate for use in the present invention. Suitable pharmaceutical materials include all acidic and basic drugs. Examples include drugs having basic groups such as amino groups, amido groups, guanidino groups, and heterocyclic groups. Additional examples include drugs which are carboxylic acids or amides, or which have carbonyl groups or other acidic groups.

A large percentage of the available pharmaceutical materials are capable of forming complexes with ion exchange resins. Typical pharmaceuticals include but are not limited to oxycodone hydrochloride, oxycodone terephthalate, chlorpheniramine maleate, codeine, morphine, dextromethorphan, phenylpropanolamine, pseudoephedrine, hydrocodone bitartrate, dihydrocodeine, salts and derivatives of morphine, methylephedrine, tramadol hydrochloride, ephedrine, paramino salicylic acid, phentermine, pilocarpine, metoclopramide and theophylline. Other possible drugs for use in the invention include all alpha-adrenergic agonists and blockers; beta-adrenergic agonists and blockers; narcotic and non-narcotic analgesics; anorexics; antiallergics; antiamebics; antianginals; antiasthmatics; antibacterials such as aminoglycosides, carbacephems, carbapenems, cephalosporins, cephamycins, penicillins, polypeptides, tetracyclines, quinolones, and sulfonamides; anticholinergics; antidepressants; antifungals; nonsteroidal anti-inflammatories; antispasmodics; antiulceratives; antivirals; anxiolytics; calcium channel blockers; dopamine receptor agonists and antagonists; narcotic antagonists; protease inhibitors; respiratory stimulants; retroviral protease inhibitors; reverse transcriptase inhibitors; sedatives such as benzodiazepine derivatives; and cerebral, coronary, and peripheral vasodilators. Of course, depending on the pKa of the pharmaceutical, either an anionic or cationic exchange resin will be selected. In some cases, an amphoteric resin may be used depending on the physicochemical properties of the pharmaceutical, i.e., pKa as well as binding constants.

Many other pharmaceutical materials may be employed in the sustained release particles and process of this invention. Numerous such examples are known in the art and particularly in the aforementioned U.S. Pat. No. 2,990,332 to Keating that is incorporated herein by reference.

The sustained release particles of this invention typically contain from about 5% to about 80% by weight of a pharmaceutical material. A more preferred amount of pharmaceutical content of the particles of this invention is from about 10% to about 60% by weight and a more preferred range of pharmaceutical content of the particles of this invention is from about 10% to about 50% by weight.

In the process of this invention, a suspension of the ion exchange resin is formed and the pharmaceutical material is applied to the resin particle suspension. Alternatively, the ion exchange resin may be added to a suspension or solution of the pharmaceutical material. Ionic forces provide complexation of the pharmaceutical material with the resin.

The prepared resin-pharmaceutical complex is then ready to be introduced to a diffusion barrier material in a low or high shear granulation process employing a granulation vehicle. The granulation vehicle includes water and mixtures of water and alcohol. The release profile of the sustained release particles of the invention may be modified by varying the amount of alcohol in the mixture. In one embodiment, the diffusion barrier material is introduced into the granulation apparatus first with an aqueous granulation vehicle wherein some hydration of the diffusion barrier material takes place.

After the diffusion barrier material has been added to the granulation device, the above noted resin-pharmaceutical complex is combined with the diffusion barrier material. While not bound by any theory, it is believed that shear forces allow binding of the resin-pharmaceutical complex into and on the surface of the particulate diffusion barrier material. The diffusion barrier material is not required to completely cover particles of the resin-pharmaceutical complex.

Preferably, a high shear granulation process is employed. Typical high shear granulators useful in the process of this invention are Model VG-5 granulator or Model VG-25; both manufactured by Powrex Corp.

Any number of diffusion barrier layer materials can be employed in the sustained release particles of this invention. Such materials of course must be inert to the pharmaceutical material and non-toxic. Typical diffusion barrier materials include but are not limited to ethylcellulose and microcrystalline cellulose or mixtures thereof, polymethacrylates and polyacrylates and copolymers thereof, chitosan, starch and lactose or combinations of starch or lactose with microcrystalline cellulose. Examples of polymethacrylates are material sold under the trade name Eudragit® by Rohm Pharma GmbH. In one embodiment, the diffusion barrier material is a combination of ethylcellulose and microcrystalline cellulose. Typically, the nominal mean particle size of the diffusion barrier material is in the range of from about 20 to about 180 microns although other size ranges may be employed.

After granulation, the product is dried and sized by typical means. Any suitable drying means such as a fluid-bed dryer may be employed. Further treatment of the product may occur if desired. The granulation process may provide particles of irregular shape. In some instances, a spherical shape is desired. To make the product into spheres, the product from the granulation process may be extruded into small thin rods. The rods are typically produced by forcing the material through a die containing holes in the range of from about 0.5 mm to about 5 mm and made into spheres by typical means. One such means to provide spherical shaped particles is to introduce the rods into a spheronizer. The spheres are then sieved to a desired size range. In another embodiment, the sustained release pharmaceutical particles can be provided in spherical form after granulation is completed, without performing a further step for spheronization. For example, in granulating with a high shear granulator, a controlled granule growth is accompanied by further densification of the granules and embedding of the resin-pharmaceutical complex within the diffusion barrier material. Following the drying of the granules, no further treatment is necessary to provide an extended release of the pharmaceutical material.

The sustained release particles of this invention may be included in a variety of dosage forms such as powders, capsules, liquid suspensions or other conventional dosage forms. Of particular utility is the hard or soft gelatin capsule combining a combination of sustained release particles carrying differing pharmaceutical materials.

The following examples are intended to illustrate the present invention and are not to limit the claims in any manner. All of the percentages are by weight unless otherwise indicated.

EXAMPLE 1

One thousand grams of ion-exchange resin AMBERLITE IRP69, marketed by Rohm and Haas Chemical Co., having a US Std. Mesh size in the range of 100 to 400 were suspended in 2 liters of deionized water. Hydrocodone bitartrate, 600 g, was dissolved in 6 liters of deionized water and added to the aqueous resin suspension with stirring. The mixture was stirred for 2 hours at room temperature. The suspension was then filtered through a Buchner funnel and washed three times with 1 liter of deionized water each. The washed filter cake was dried in a fluid-bed drier to a final moisture content of about 10%. The dry powder (hydrocodone-resin complex; HC-resinate) was analyzed by HPLC and determined to have a hydrocodone content equivalent to 45% by weight of hydrocodone bitartrate.

A high shear granulator was fitted with a 5-liter bowl and charged with 100 g of HC-resinate from above. Deionized water (100 g) was sprayed onto the complex and mixed for about 5 minutes. One hundred grams of ethylcellulose powder was added to the granulating bowl and mixed for 5 minutes followed by the addition of 200 g of microcrystalline cellulose sold under the trade name Avicel PH-101 (product of FMC Corp.) and blended for an additional 6 minutes. The wet mixture was granulated with 339.9 g of deionized water. The wet granules were divided into two portions (Portions A and B).

Portion A was sieved through a US Std. Mesh #6 screen and fluid-bed dried. The dry granules were sieved through US Std. Mesh #16 and #20 screens and marked as Sample A. HPLC analysis of the fraction showed that the hydrocodone content was equivalent to 8.9% by weight of hydrocodone bitartrate. A dissolution test was performed in 0.1N HCl (Paddles; 100 rpm; 500 ml; N=3) and the data reported in Table 1 below.

The unsieved Portion B was extruded into thin rods using an LCI Laboratory Dome Granulator (model DG-L1) employing a 0.8 mm die. The thin rods were made into spheres using a Marumerizer (manufactured by Fuji Paukal Co., Ltd). The spheres were dried by means of a fluid-bed dryer. The spherical particles thus produced were sieved and the US Std. Mesh −16+20 fraction was analyzed by HPLC showing the granules contained 8.9% by weight hydrocodone bitartrate. Portion B was marked as Sample B. A dissolution test was performed by the procedure indicated above for this portion and the data obtained are presented in Table 1 below.

TABLE 1

| Time (minutes) | SAMPLE NO. | | | |
|---|---|---|---|---|
| | A | | B | |
| | Manufacturing Process | | | |
| | Granulation | | Extrusion/Marumerization | |
| | Dissolution Data | | | |
| | Cumulative % Dissolved | | Cumulative % Dissolved | |
| | Mean | SD | Mean | SD |
| 15 | 14.0 | 1.9 | 12.3 | 0.9 |
| 30 | 22.9 | 1.8 | 20.6 | 0.5 |
| 60 | 34.6 | 1.0 | 31.0 | 0.6 |
| 120 | 48.0 | 0.3 | 43.8 | 0.9 |
| 180 | 58.3 | 0.3 | 53.3 | 0.8 |

Sustained release ion-exchange resin complexes can be achieved by a granulation process alone or by extrusion-marumerization process as shown by the data in Table 1 above. Such processes are achieved without use of a coating process or organic solvent in any step.

EXAMPLE 2

A batch of hydrocodone-resin complex was prepared as in Example 1 with the exception that the wet cake was not dried but was in the wet state when introduced into the granulation process. The wet hydrocodone-resin complex, 183.3 g, moisture content of 45.43%, was granulated with 200 g of ethylcellulose (Ethocel Standard 10FP Premium marketed by Dow Chemical Co.), 100 g microcrystalline cellulose (Avicel PH-101) and 228.42 g deionized water. The wet granules were sieved through a US Std. Mesh #10 screen and dried in a fluid-bed drier to a final moisture content of 4.2% and marked Sample C. The dry granules were then sieved through US Std. Mesh #16 and #20 screens. The −16+20 fractions were analyzed by HPLC and by dissolution test as in Example 1. The data are reported in Table 2 below.

EXAMPLE 3

The procedure of Example 2 was repeated except that the granulation matrix was only 300 g of Avicel PH-101 together with 181.8 g of wet hydrocodone-resin complex. The final product was marked Sample D. The −16+20 fractions were analyzed by HPLC and by dissolution test as in Example 1. The data are reported in Table 2 below.

EXAMPLE 4

The procedure of Example 2 was repeated with the exception that the granulation matrix was 200 g of Avicel PH-101, 200 g of ethylcellulose and 181.8 g of the wet hydrocodone-resin complex. The final product was marked Sample E. The dry granules were sieved as in Example 2 and the −16+20 fractions were analyzed by HPLC and by the dissolution test as described in Example 1. The data are presented in Table 2 below.

TABLE 2

| Lot No | Sample C | | Sample D | | Sample E | |
|---|---|---|---|---|---|---|
| Hydrocodone Content | 9.7% | | 8.4% | | 8.7% | |
| Dissolution Data-Cumulative % Released | | | | | | |
| Time (minutes) | Mean | SD | Mean | SD | Mean | SD |
| 15 | 13.2 | 1.4 | 20.4 | 2.8 | 17.9 | 0.7 |
| 30 | 22.3 | 1.6 | 29.8 | 4.0 | 28.0 | 1.0 |
| 60 | 35.6 | 3.3 | 40.4 | 3.7 | 40.4 | 1.6 |
| 120 | 49.8 | 3.1 | 53.7 | 4.0 | 55.3 | 2.0 |
| 180 | 58.1 | 2.9 | 62.1 | 3.1 | 63.7 | 0.9 |

Varying the matrix suitably may modify release profile.

Example 5

Particles of ion exchange resin AMBERLITE IRP69, 1.5 kg having a size range of US Std. Mesh #100-#400 were suspended in 6 kg of USP water. Hydrocodone bitartrate, 900 g was added in one step to the resin suspension with stirring. The mixture was stirred for 1 hour at room temperature, filtered through a sintered glass funnel, and washed three times with 1.5 kg of USP water each.

To a 25-liter bowl of a Powrex Hi-Shear granulator were charged 2.55 kg of microcrystalline cellulose, Avicel PH-101. The Avicel was wetted with 0.96 kg of USP water. Granulation parameters were set as follows: Main blade: 200 rpm, Cross-screw: 400 rpm, Water addition rate: 97 g/minute. After all the water had been added, 0.806 kg of the wet HC-resinate cake from above was added and mixed for 6 minutes. The mixture was granulated with 1.316 kg of USP water. Granulation parameters were: Main Blade: 60 rpm; Cross-screw: 600 rpm; Water addition rate: 133 g/minute. After all the water had been added, the mixture was blended for an additional 6 minutes. The resulting wet granules were sieved through a US Std. Mesh #4 screen and dried in a fluid-bed drier to a final moisture content of 4.70%. The dry granules were first sieved through a US Std. Mesh #16 screen and then with a #40 screen. The yield of the −16+40 fractions was 2.081 kg and the combined fractions were analyzed by HPLC for hydrocodone content. The product was marked Sample F. The data for six replicate tests of the dissolution test as described in Example 1 above was performed and the data for this product are presented in Table 3 below.

EXAMPLE 6

Particles of ion-exchange resin AMBERLITE 1RP69 (1.5 kg; US Std. Mesh #100-#400) were suspended in 6 kg of USP water. Hydrocodone bitartrate, 900 g was added all at once to the resin suspension with stirring. The mixture was stirred for 1 hour at room temperature, filtered through a sintered glass funnel, washed three times with 1.5 kg of USP water each.

To a 25-liter bowl of a Powrex Hi-Shear granulator were charged 2.250 kg of microcrystalline cellulose (Avicel PH-101). The Avicel was wetted with 0.850 kg of USP water and granulated. Granulation parameters were: Main blade: 200 rpm; Cross-screw: 400 rpm; Water addition rate: 87 g/minute. After all the water had been added, 1.391 kg of the wet cake from above was added and the mixture was blended for an additional 6 minutes. The mixture was granulated with 1.491 kg of USP water. The granulation parameters were: Main blade: 60 rpm; Cross-screw: 600 rpm; Water addition rate: 122 g/minute. After all the water had been added, the mixture was blended for an additional 6 minutes. The resulting wet granules were sieved through a US Std. Mesh #4 screen and dried in a fluid-bed drier to a final moisture content of 3.90%. The dry granules were first sieved through a US Std. Mesh #16 screen and then with a #40 screen. The yield of the −16+40 fraction was 1.957 kg. The product was marked Sample G and analyzed by HPLC to determine the hydrocodone content. The data for six replicate tests of dissolution rate for this product are shown in Table 3 below. The tests were conducted as noted above in Example 1.

EXAMPLE 7

Particles of ion-exchange resin AMBERLITE IRP69, 1.5 kg, US Std. Mesh #100-#400, were suspended in 4 kg of USP water. The suspension was warmed to 30°-35° C. Chlorpheniramine maleate, 300 g, was added all at once to the resin suspension with stirring. The mixture was stirred for 1 hr. at 30°-35° C., filtered through a sintered glass funnel and washed three times with 1.5 kg of USP water each time to provide a wet cake (CP-resinate).

The 25-liter bowl of a Powrex Hi-Shear granulator was charged with 1.5 kg of microcrystalline cellulose, Avicel PH-101. The Avicel was wetted with 0.570 kg of USP water. Granulation parameters were: Main blade: 80 rpm; Cross-screw: 400 rpm; Water addition rate: 58 g/minute. After all the water had been added, 3.151 kg of the wet cake, CP-resinate, from the above were added and mixed for 6 minutes. The mixture was granulated with 1.651 kg of USP water. Granulation parameters were: Main blade: 60 rpm; Cross-screw: 600 rpm; Water addition rate: 102 g/minute. After all the water had been added, the mixture was blended for an additional 6 minutes. The resulting wet granules were sieved through a US Std. Mesh #4 screen and dried in a fluid-bed drier to a final moisture content of 5.31%. The dry granules were first sieved through a US Std. Mesh #16 screen and then with a #40 screen. The yield of the −16+40 fraction was 1.450 kg with a moisture content of 5.31%. The product was marked Sample H and the −16+40 fraction was analyzed by HPLC for chlorpheniramine content. The data for six replicate tests of dissolution rate for this product are shown in Table 3 below. The tests were conducted as noted above in Example 1.

EXAMPLE 8

Particles of ion-exchange resin AMBERLITE IRP69 (1.5 kg; US Std. Mesh #100-#400) were suspended in 4 kg of USP water. The suspension was warmed to 30°-35° C. Chlorpheniramine maleate (300 g) was added all at once to the resin suspension with stirring. The mixture was stirred for 1 hour at 30°-35° C., filtered through a sintered glass funnel, washed three times with 1.5 kg of USP water each.

The 25-liter bowl of a Powrex Hi-Shear granulator was charged with 2.250 kg of microcrystalline cellulose, Avicel PH-101. The Avicel was wetted with 0.850 kg of USP water. Granulation parameters were: Main blade: 200 rpm; Cross-screw: 400 rpm; Water addition rate: 86 g/minute. After all the water had been added, 1.522 kg of the wet cake from the above was added and mixed for 6 minutes. The mixture was granulated with 1.622 kg of USP water. Granulation parameters were: Main blade: 60 rpm; Cross-screw: 600 rpm; Water addition rate: 122 g/minute. After all the water had been added, the mixture was blended for an additional 6 minutes. The resulting wet granules were sieved through a US Std. Mesh #4 screen and dried in a fluid-bed drier to a final moisture content of 4.40%. The dry granules were first sieved through a US Std. Mesh #16 screen and then with a #40 screen. The yield of the −16+40 fraction was 2.105 kg. The product was marked as Sample I and subjected to HPLC analysis for chlorpheniramine content. The data for six replicate tests of dissolution rate for this product are shown in Table 3 below. The tests were conducted as noted above in Example 1.

TABLE 3

| Product | SAMPLE F | | SAMPLE G | | SAMPLE H | | SAMPLE I | |
|---|---|---|---|---|---|---|---|---|
| Active Drug | Hydrocodone | | | | Chlorpheniramine | | | |
| Content | 10% | | 6.3% | | 8.4% | | 4.3% | |
| Dissolution Data-Cumulative % Released | | | | | | | | |
| Time (hrs.) | Mean | SD | Mean | SD | Mean | SD | Mean | SD |
| 0.25 | 32.8 | 2.7 | 21.5 | 1.3 | 40.7 | 7.1 | 21.6 | 1.5 |
| 0.5 | 45.4 | 4.0 | 32.3 | 1.6 | 51.4 | 5.3 | 30.9 | 1.5 |
| 1 | 58.3 | 4.6 | 44.4 | 2.0 | 61.0 | 5.8 | 40.5 | 2.6 |
| 2 | 70.5 | 4.8 | 57.4 | 2.4 | 68.3 | 4.7 | 50.8 | 2.8 |
| 3 | 76.9 | 4.1 | 64.8 | 2.3 | 71.6 | 3.8 | 56.7 | 2.9 |
| 6 | 84.4 | 3.4 | 76.2 | 1.9 | 74.7 | 3.1 | 66.1 | 2.6 |
| 8 | 86.7 | 2.7 | 80.4 | 1.9 | 75.6 | 2.6 | 69.6 | 2.4 |

EXAMPLE 9

Hydrocodone polistirex was prepared by mixing 4.00 kg of hydrocodone bitartrate with 4.76 kg of ion-exchange resin particles (ABMERLITE IRP69; US Std. Mesh #100-#400) suspended in USP water at about 70° C. The resulting suspension was centrifuged and the product washed with USP water. The wet cake was dried and sieved through a US Std #30 mesh screen. The hydrocodone content of the dried product was equivalent to approximately 56% by weight of hydrocodone bitartrate.

A Powrex Hi-Shear granulator fitted with a 50-liter bowl was charged with 6.480 kg of microcrystalline cellulose (Avicel PH-101). USP water (2.398 kg) was added to the Avicel, with the main blade of the granulator at 200 rpm and the cross-screw at 400 rpm. The water addition rate was 0.2 kg/minute. Hydrocodone polistirex (0.720 kg) prepared as above was then added to the granulator and mixed with the Avicel for 6 minutes. The granulator parameters were: Main blade: 200 rpm; Cross-screw: 400 rpm. USP water (3.942 kg) was added to the mixture in the granulator at a rate of 0.2 kg/minute. The granulator parameters were: Main blade: 60 rpm; Cross-screw: 600 rpm. After all the water had been added, the wet mass was blended for an additional 6 minutes. The granulator parameters were: Main blade: 60 rpm; Cross-screw: 600 rpm during the additional 6 minutes. The product was discharged from the granulator and sieved through a US Std. Mesh #4 screen to yield 13.31 kg of wet granules. Approximately 3.3 kg of the sieved wet granules were spheronized using a Marumerizer fitted with a 4-liter bowl and a friction plate with 2-mm grooves. The plate speed and marumerization times were about 400 rpm and 4 minutes respectively. The wet spherical granules were then dried in a fluid-bed processor and the final moisture content was found to be 2.0%. The marumerization step was repeated until all the wet granules had been spheronized. The granulation step was repeated several times to make several kg of the dry HP granules. All the dry HP granules were combined and sieved through a US Std. Mesh #18 screen. A representative sample of the final product was analyzed by HPLC for hydrocodone content. The hydrocodone content was determined to be equivalent to 5.5% by weight. The data for six replicate tests of dissolution rate for this product are shown in Table 4 below. The tests were conducted as noted in Example 1.

EXAMPLE 10

Chlorpheniramine polistirex was prepared by mixing 3.12 kg of chlorpheniramine maleate with 26.00 kg of ion-exchange resin particles (AMBERLITE IRP69; US Std. Mesh #100-#400) suspended in USP water at about 30° C. The resulting suspension was centrifuged and the product washed with USP water. The wet cake was dried and sieved through a US Std #30 mesh screen. The chlorpheniramine content of the dried product was equivalent to approximately 11% by weight.

A Powrex Hi-Shear granulator was fitted with a 50-liter bowl and charged with 3.960 kg of microcrystalline cellulose (Avicel PH-101). USP water (1.465 kg) was added to the Avicel, with the main blade of the granulator at 200 rpm and the cross-screw at 400 rpm. The water addition rate was 0.2 kg/minute. Chlorpheniramine polistirex (3.240 kg) prepared as above was then added to the granulator and mixed for 6 minutes. The granulator parameters were: Main blade: 200 rpm; Cross-screw: 400 rpm. USP water (4.996 kg) was added at a rate of 0.2 kg/minute. The granulator parameters were: Main blade: 60 rpm; Cross-screw: 600 rpm. After all the water had been added, the wet mass was blended for an additional 6 minutes. The granulator parameters were: Main blade: 60 rpm; Cross-screw: 600 rpm. The product was discharged from the granulator and sieved through a US Std. Mesh #4 screen to yield 13.55 kg of wet granules. Approximately 3.3 kg of the sieved wet granules were spheronized using a Marumerizer fitted with a 4-liter bowl and a friction plate with 2-mm grooves. The plate speed and the marumerization time were about 1000 rpm and 5 minutes respectively. The wet spherical granules were then dried in a fluid-bed processor and the final moisture content was found to be 4.3%. The marumerization step was repeated until all the wet granules had been spheronized. The granulation step was repeated several times to make several kg of the dry CP granules. All the CP granules were combined and sieved through a US Std. Mesh #18 screen. A representative sample of the final product was analyzed by HPLC for chlorpheniramine content. The chlorpheniramine content was determined to be equivalent to 5.2% by weight. The data for six replicate tests of dissolution rate for this product are shown in Table 4 below. The tests were conducted as noted in Example 1.

TABLE 4

| | Example 9 | | Example 10 | |
|---|---|---|---|---|
| Active Drug | Hydrocodone | | Chlorpheniramine | |
| Content | 5.5% | | 5.2% | |
| Dissolution Data-Cumulative % Released | | | | |
| Time (hrs.) | Mean | SD | Mean | SD |
| 0.25 | 14.4 | 2.8 | 29.3 | 2.6 |
| 0.5 | 25.6 | 3.6 | 39.9 | 2.6 |
| 1 | 39.0 | 4.0 | 49.6 | 3.3 |
| 2 | 54.4 | 3.9 | 59.8 | 4.0 |
| 3 | 64.2 | 3.6 | 63.4 | 3.5 |
| 6 | 78.7 | 2.1 | 68.7 | 3.0 |
| 8 | 85.0 | 1.6 | 70.5 | 2.7 |

Oral dosage forms were prepared by filling gelatin capsules with the HP and CP granules made as above.

Decreasing the level of resin-drug complex in the granulation matrix may slow release of the pharmaceutical. Different pharmaceutical agents may have different release rates due to the strength of the pharmaceutical-resin complex.

Although the invention has been described in terms of specific embodiments which are set forth in considerable detail, it should be understood that this description is by way of illustration only and that the invention is not necessarily limited thereto since alternative embodiments and operating techniques will become apparent to those skilled in the art in view of the disclosure. Accordingly, modifications are contemplated which can be made without departing from the spirit of the described invention.

What is claimed is:

1. A non-coated, sustained release pharmaceutical composition consisting of a plurality of granules, the granules consisting of:
   (i) about 10% to about 60% by weight of a non-coated complex particulate consisting of styrene-divinylbenzene sulfonic acid cationic exchange resin particles and different pharmaceutically active materials complexed with the ion exchange resin particles, the pharmaceutically active materials being selected from the group consisting of oxycodone hydrochloride, tramadol hydrochloride, dextromethorphan, hydrocodone bitartrate, chlorpheniramine maleate, codeine, morphine or morphine salt, hydrocodone, phenylpropanolamine, pseudoephedrine, dihydrocodeine, methylephedrine, ephedrin, paramino salicylic acid, phentermine, pilocarpine, metoclopramide and theophylline, wherein each of the different pharmaceutically active materials is complexed with different ion exchange resin particles; and,
   (ii) a non-coated, granulated water-insoluble matrix consisting of microcrystalline cellulose, wherein the non-coated, complex particulate is embedded into the non-coated, granulated water-insoluble matrix of microcrystalline cellulose, and further wherein the non-coated, granulated water-insoluble matrix of microcrystalline cellulose sustains release of the different pharmaceutically active materials from the non-coated, complex particulate.

2. The non-coated composition of claim 1 wherein one of the pharmaceutically active materials is hydrocodone bitartrate.

3. The non-coated composition of claim 2 wherein one of the pharmaceutically active materials is chlorpheniramine maleate.

4. The non-coated composition of claim 1 wherein the granules consist of about 10% to about 50% by weight of the non-coated complex particulate.

5. A process for preparing a non-coated, sustained release pharmaceutical composition comprising a plurality of granules, the process comprising:
   A. forming a suspension of ion exchange resin particles together with a pharmaceutically active material under complexing conditions thereby forming a non-coated complex particulate comprising the ion exchange resin and the pharmaceutically active material;
   B. introducing a water-insoluble particulate diffusion barrier material and the non-coated complex particulate of step A into a granulator with a granulating vehicle whereby the non-coated complex particulate and the water-insoluble diffusion barrier material particulate are granulated to embed the non-coated complex particulate into a non-coated, water-insoluble matrix of the water-insoluble diffusion barrier material particulate, wherein (i) the water-insoluble diffusion barrier material particulate is selected from the group consisting of ethylcellulose, microcrystalline cellulose, a polymethacrylate, a polyacrylate, chitosan, starch, or a combination thereof, and (ii) the non-coated, granulated water-insoluble matrix of the water-insoluble diffusion barrier material particulate sustains release of the pharmaceutically active material from the non-coated complex particulate.

6. The process of claim 5 wherein the granulating vehicle is selected from the group consisting of water and mixtures of water and alcohol.

7. The process of claim 5 wherein the granulating vehicle comprises water.

8. The process of claim 5 wherein the pharmaceutically active material is an analgesic.

9. The process of claim 5 wherein the water-insoluble diffusion barrier material particulate consists of microcrystalline cellulose.

10. The process of claim 5 wherein the water-insoluble diffusion barrier material particulate consists of microcrystalline cellulose and ethylcellulose.

11. The process of claim 5 wherein the pharmaceutically active material is a member of the class of treatments selected from the group consisting of alpha-adrenergic agonists and blockers; beta-adrenergic agonists and blockers; narcotic and non-narcotic analgesics; anorexics; antiallergics; antiamebics; antianginals; antiasthmatics; antibacterials; anticholinergics; antidepressants; antifungals; nonsteroidal anti-inflammatories; antispasmodics; antiulceratives; antivirals; anxiolytics; calcium channel blockers; dopamine receptor agonists and antagonists; narcotic antagonists; protease inhibitors; respiratory stimulants; retroviral protease inhibitors; reverse transcriptase inhibitors; sedatives; and cerebral, coronary, and peripheral vasodilators.

12. The process of claim 5 wherein the pharmaceutically active material is selected from the group consisting of oxycodone hydrochloride, tramadol hydrochloride, chlorpheniramine maleate, dextromethorphan, codeine, morphine or morphine salt, hydrocodone bitartrate, phenylpropanolamine, pseudoephedrine, dihydrocodeine, methylephedrine, ephedrin, paramino salicylic acid, phentermine, pilocarpine, metoclopramide and theophylline.

13. The process of claim 5 wherein the ion exchange resin is selected from the group consisting of functionalized resins derived from divinylbenzenes, styrenic, methacrylic, methacrylamide, acrylic, acrylamide, carbacrylic, phenol-formaldehyde, polyhydroxy resins, polycarboxylic, carboxyvinyl, cellulosic, dextran, zeolite, fuller's earth, peat, lignite, permutite, dolomite, iron oxide hydrate gel, zirconium oxide hydrate gel, activated carbon, zwitterionic and amphoteric resins.

14. The process of claim 5 wherein the initial resin particle size is in the range of US Std. Mesh from about #10 to about #400.

15. The process of claim 5 wherein the pharmaceutically active material is hydrocodone bitartrate.

16. The process of claim 5 wherein the pharmaceutically active material is chlorpheniramine maleate.

17. The process of claim 5 further including the step of spheronization after granulation.

18. The process of claim 17 wherein the pharmaceutically active material is hydrocodone bitartrate.

19. The process of claim 17 wherein the pharmaceutically active material is chlorpheniramine maleate.

20. The process of claim 5, further comprising: (i) repeating steps A and B using a different pharmaceutically active material, in order to obtain a second plurality of granules different from the first; and, (ii) combining the two sets of granules to form a mixture thereof.

21. The process of claim 20, wherein a first pharmaceutically active material is hydrocodone bitartrate, and a second pharmaceutically active material is chlorpheniramine maleate.

22. The process of claim 5, further comprising placing the plurality of granules resulting from step B in a capsule or liquid suspension for administration to a mammal in need thereof.

23. A non-coated, sustained release pharmaceutical composition consisting of:
(A) a plurality of granules consisting of (i) about 10% to about 60% by weight of a non-coated complex particulate consisting of styrene-divinylbenzene sulfonic acid cationic exchange resin particles complexed with hydrocodone; and, (ii) a non-coated, granulated water-insoluble matrix of a water insoluble particulate diffusion barrier material selected from the group consisting of microcrystalline cellulose, a polymethacrylate, a polyacrylate, chitosan, starch, or a combination thereof, wherein the non-coated, complex particulate of styrene-divinylbenzene sulfonic acid cationic exchange resin particles and hydrocodone is embedded into the non-coated, granulated water-insoluble matrix, and further wherein the non-coated, granulated water-insoluble matrix sustains release of the hydrocodone from the non-coated, complex particulate; and,
(B) a plurality of granules consisting of (i) about 10% to about 60% by weight of a non-coated complex particulate consisting of styrene-divinylbenzene sulfonic acid cationic exchange resin particles complexed with chlorpheniramine; and, (ii) a non-coated, granulated water-insoluble matrix of a water insoluble particulate diffusion barrier material selected from the group consisting of microcrystalline cellulose, a polymethacrylate, a polyacrylate, chitosan, starch, or a combination thereof, wherein the non-coated, complex particulate of styrene-divinylbenzene sulfonic acid cationic exchange resin particles and chlorpheniramine is embedded into the non-coated, granulated water-insoluble matrix, and further wherein the non-coated, granulated water-insoluble matrix sustains release of the chlorpheniramine from the non-coated, complex particulate.

* * * * *